United States Patent [19]

Groux

[11] 4,273,110
[45] Jun. 16, 1981

[54] ULTRAVIOLET ENDOSCOPE

[76] Inventor: Jean Groux, 15 Av. de Lenine, Morsang sur Orge, France, 91390

[21] Appl. No.: 56,703

[22] Filed: Jul. 11, 1979

[30] Foreign Application Priority Data

Jul. 13, 1978 [FR] France .............................. 78 20993

[51] Int. Cl.³ .............................................. A61B 1/06
[52] U.S. Cl. ...................................................... 128/6
[58] Field of Search ...................................... 128/3-9; 362/804

[56] References Cited

U.S. PATENT DOCUMENTS

| 1,643,718 | 9/1927 | Loeck | 128/6 |
| 3,456,641 | 7/1969 | Yokota et al. | 128/4 |
| 3,858,577 | 1/1975 | Bass et al. | 128/8 |
| 4,072,147 | 2/1978 | Hett | 128/6 |
| 4,195,329 | 3/1980 | Woog | 362/804 |

Primary Examiner—John D. Yasko
Attorney, Agent, or Firm—Lerner, David, Littenberg & Samuel

[57] ABSTRACT

An endoscope is disclosed for examining minute details at an inaccessible location including an image transmitting conduit, a light guide for transmitting light from a source of ultraviolet and visible light to the remote end of the endoscope, and a conduit for delivering a substance which becomes fluorescent under the influence of ultraviolet light to that end of the endoscope. Preferably the endoscope includes a retractable filter for visible light which can be placed in the light guide to prevent visible light from passing through the light guide.

9 Claims, 1 Drawing Figure

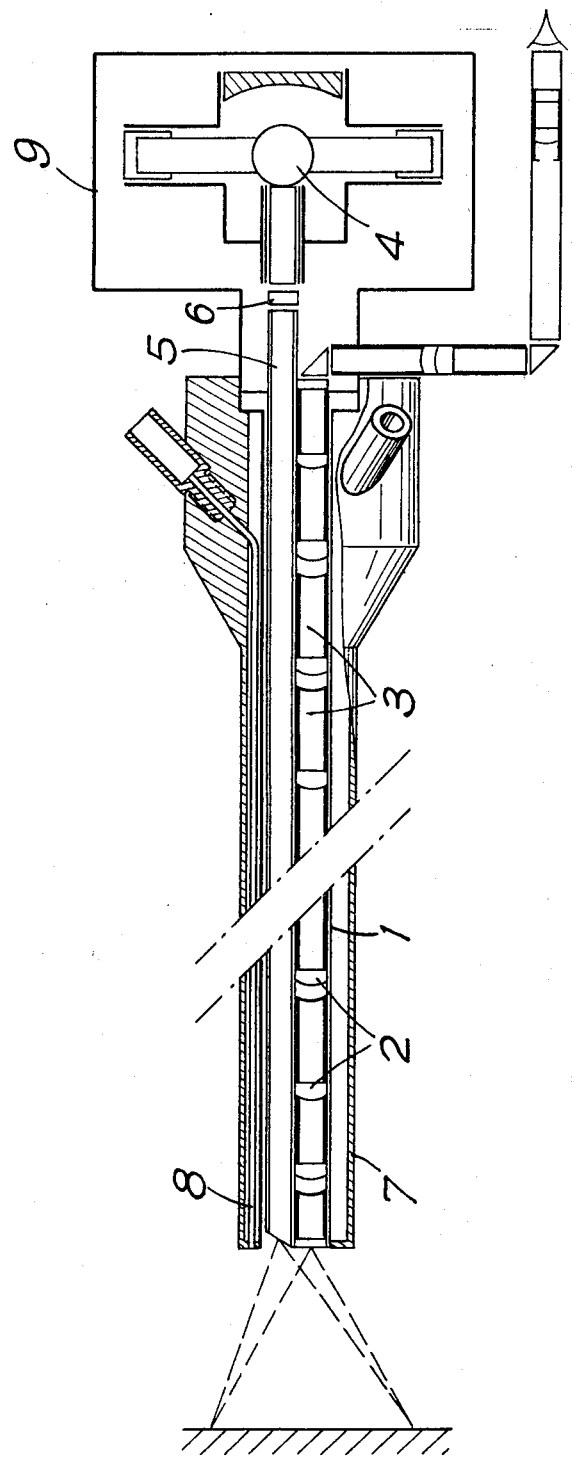

ULTRAVIOLET ENDOSCOPE

FIELD OF THE INVENTION

The invention relates to an endoscope permitting to visualize very small details inside cavities that are only accessible through an orifice of small diameter.

BACKGROUND OF THE INVENTION

A currently used endoscope lights up the surface to be examined, perpendicularly thereto, thereby preventing visualization small details, which are best observed only under a grazing light.

SUMMARY OF THE INVENTION

In accordance with the present invention these disadvantages have been overcome by the use of an endoscope comprising an optical conduit or image transmitting member for transmitting an image from a first inaccessible location to a second viewing location, light guide means for transmitting light from a source of ultraviolet and visible light to that first location, and a conduit for delivering a substance which becomes flourescent under the influence of ultraviolet light to the first location.

BRIEF DESCRIPTION OF THE DRAWING

Other characteristics of the invention will become evident from the following description given by way of example and non-restrictively, reference being made to the accompanying drawing in which:

The one and only FIGURE is a cross-sectional view of an endoscope according to the invention.

DETAILED DESCRIPTION

The endoscope according to the invention and shown in the drawing comprises an optical conduit for the transmission of images composed of lenses 2 separated by spacers 3. Said optical conduit is designed with a double angular member to allow the accurate positioning of the light source 4 in the axis of the light guide 5 which is constituted by a quartz tube permitting the transmission of the visible and ultraviolet radiation from the source, a filter 6 between said source and said light guide stopping the visible light radiated from the source.

The conduit 1 and the guide 5 are enclosed in a sheath 7 in which are provided three conduits 8 for bringing and spraying a product on the part to be examined, which product becomes fluorescent under an ultraviolet lighting. One of these three conduits is reserved for a gaseous product, another for a liquid product and the third for a pulverulent product.

The light source 4 is fitted on the sheath 7 and is mounted in a casing 9, a gas flow cooling the source of which the power supply is located outside the casing.

The filter 6 is retractable and is only used to observe details in ultraviolet. Indeed, when using the endoscope, the operator searches for the portion of the part to be examined, by lighting with visible light without interposing the filter 6; once he has located the said portion he sprays the product via one of the conduits 8 and gives ultraviolet lighting only, using the filter 6 so that the fluorescent details are not blurred by the visible light.

The invention is not limited to the embodiments hereinabove described, and various modifications may be made thereto without departing from its scope.

What is claimed is:

1. An endoscope for examining detailed images from a first inaccessible location to a second viewing location, said endoscope comprising an image transmitting member for transmitting an image from said first location to said second location, light guide means for transmitting light produced by a source of ultraviolet and visible light to said first location, and conduit means substantially coextensive with said light guide means for delivering a substance which becomes flourescent under the influence of ultraviolet light to said first location.

2. The endoscope of claim 1 including filter means associated with said light guide means for preventing visible light produced by said light source from being transmitted to said first location.

3. The endoscope of claim 2 wherein said filter means is retractable so that said light transmitted to said first location may alternately comprise said ultraviolet light and a combination of said ultraviolet light and said visible light.

4. The endoscope of claim 1 wherein said image transmission member includes double angular means for altering the direction of said image being transmitted therein so as to displace said second viewing location from the path of said light guide means.

5. The endoscope of claim 4 wherein said light source is located directly in the path of said light guide means.

6. The endoscope of claim 1 wherein said image transmission member and said light guide means are enclosed in a sheath and said sheath includes said conduit means.

7. The endoscope of claim 6 wherein said conduit means comprises a plurality of conduits for delivery of said substance.

8. The endoscope of claim 7 wherein said plurality of conduits comprises three conduits, for delivery of a gaseous substance a liquid substance, and a pulverulent substance, respectively.

9. The endoscope of claim 1 wherein said light guide means comprises a quartz tube.

* * * * *